United States Patent [19]

Creger

[11] Patent Number: 5,041,640

[45] Date of Patent: Aug. 20, 1991

[54] PROCESS FOR MONO-, DI-, TRISUBSTITUTED ACETIC ACIDS

[75] Inventor: Paul L. Creger, Ann Arbor, Mich.

[73] Assignee: Warner-Lambert Company, Morris Plains, N.J.

[21] Appl. No.: 585,741

[22] Filed: Sep. 20, 1990

[51] Int. Cl.$^5$ .................. C07C 59/68; C07C 53/00
[52] U.S. Cl. .................................. 562/471; 562/606
[58] Field of Search ........................... 562/471, 606

[56] References Cited

U.S. PATENT DOCUMENTS 3,674,836 4/1972 Creger et al. .
3,935,234 1/1976 Reidenbacher .................. 562/471
4,126,637 11/1978 Goel et al. .
4,665,226 5/1987 Kearney .

FOREIGN PATENT DOCUMENTS 1297362 1/1970 United Kingdom .

Primary Examiner—Paul J. Killos
Attorney, Agent, or Firm—Francis J. Tinny

[57] ABSTRACT

An improved process for the preparation of mono-, di-, or trisubstituted acetic acids including 5-(2,5-dimethylphenoxy)-2,2-dimethylpentanoic acid by a novel synthesis is described where a carboxylic acid is converted to a soluble metalated magnesium or zinc carboxylate containing a ligand and subsequent alkylation of this intermediate in the presence of an alkali amide to afford the desired product in two steps.

14 Claims, No Drawings

PROCESS FOR MONO-, DI-, TRISUBSTITUTED ACETIC ACIDS

BACKGROUND OF THE INVENTION

U.S. Pat. No. 3,674,836, which is herein incorporated by reference, disclosed certain 2,2-dimethyl-ω-aryloxyalkanoic acids and salts and ester thereof.

The compounds disclosed in the above United States Patent are useful in regulating blood lipid levels and afford protection from coronary heart disease. Thus, they are useful in the treatment of atherosclerosis. Particularly valuable as a lipid regulating agent is gemfibrozil chemically known as 5-(2,5-dimethylphenoxy)-2,2-dimethylpentanoic acid.

U.S. Pat. Nos. 3,674,836, 4,126,637 and 4,665,226 disclose various processes for preparing the aforementioned compounds. The processes disclosed in U.S. Pat. Nos. 3,674,836 and 4,126,637 utilize metalated carboxylic acids.

The object of the present invention is an improved process for preparing the compounds described above by using a novel synthesis.

Further, we have unexpectedly found that metalated zinc and magnesium carboxylates form homogeneous solutions in nonpolar solvents. The present process is more conveniently performed in higher yields than the prior art processes. Thus, the present process is amenable to large-scale synthesis.

SUMMARY OF THE INVENTION

Accordingly, a first aspect of the present invention is an improved process for the preparation of a compound of Formula I

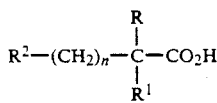

wherein R is hydrogen, lower alkyl, lower alkoxy, or aryl;
R$^1$ is hydrogen or lower alkyl;
R$^2$ is lower alkyl, aryl or aryloxy; and
n is zero or an integer of one to six which comprises:
(a) reacting a compound of Formula V

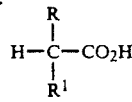

wherein R and R$^1$ are as defined above with magnesium oxide, magnesium methoxide, or zinc oxide and a ligand in a solvent to afford a compound of Formula III

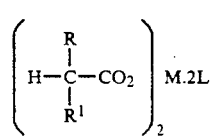

wherein M is magnesium or zinc, L is a ligand and R and R$^1$ are as defined above which may optionally be isolated if desired;
(b) reacting a compound of Formula III with a compound of Formula II

wherein R$^3$ is a leaving group and R$^2$ and n are as defined above in the presence of an alkali amide to afford, after conventional isolation, a compound of Formula I.

A second aspect of the present invention is an improved process for the preparation a compound of Formula I

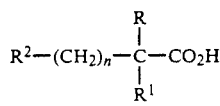

wherein R is hydrogen, lower alkyl, lower alkoxy, or aryl;
R$^1$ is hydrogen or lower alkyl;
R$^2$ is lower alkyl, aryl or aryloxy; and
n is zero or an integer of one to six which comprises:
(a) reacting a compound of Formula V

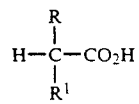

wherein R and R$^1$ are as defined above with magnesium bromide and lithium hydride or magnesium chloride and lithium hydride in a solvent to afford a compound of formula IV

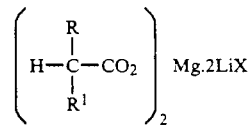

wherein X is bromide or chloride and R and R$^1$ are as defined above, which may optionally be isolated if desired:
(b) reacting a compound of Formula IV with a compound of Formula II

wherein R$^3$ is a leaving group and R$^2$ and n are as defined above in the presence of an alkali amide to afford, after conventional isolation, a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group or phenyl group substituted by one to four substituents selected from lower alkyl, lower alkoxy, lower thioalkoxy, halogen or trifluoromethyl such as, for example, benzyl, phenethyl, and the like.

Aryloxy is O-aryl as defined above for "aryl."

"Lower alkoxy" is O-alkyl of from one to six carbon atoms as defined above for "lower alkyl".

"Lower thioalkoxy" is S-alkyl of from one to six carbon atoms as defined above for "lower alkyl."

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium and the like.

A preferred compound of Formula I prepared by the improved process of the present invention is one wherein R and $R^1$ are lower alkyl; $R^2$ is aryloxy; and n is three.

Also preferred is a compound of Formula I prepared by the improved process of the present invention wherein R and $R^1$ are methyl and n is three.

A particularly preferred compound of Formula I prepared by the improved process of the present invention is:

5-(2,5-dimethylphenoxy)-2,2-dimethylpentanoic acid.

As previously described, the compounds of Formula I have been found to regulate blood lipid levels and afford protection from coronary heart disease. Thus, they are useful in the treatment of atherosclerosis.

The process of the present invention is a new, improved, economical and commercially feasible method for preparing the lipid regulating agents of Formula I. The process of the present invention is outlined in Scheme 1:

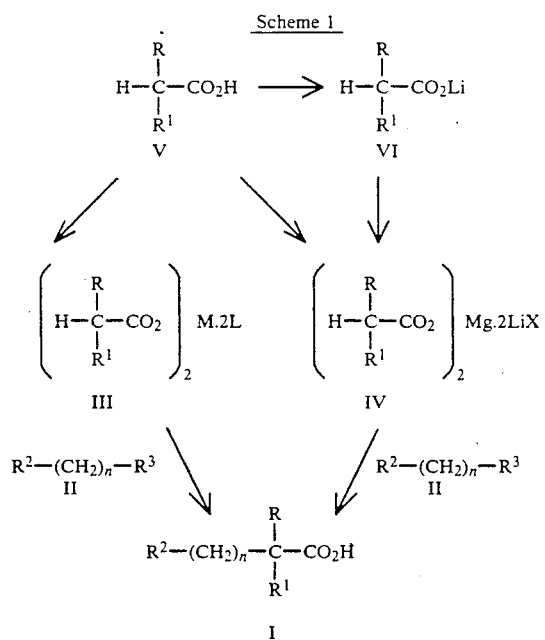

A compound of Formula III wherein R is hydrogen, lower alkyl, lower alkoxy, or aryl; $R^1$ is hydrogen or lower alkyl; M is magnesium or zinc; and L is a ligand such as, for example, tetramethylethylenediamine, tetrahydrofuran, pyridine, and the like is prepared by reacting a compound of Formula V wherein R and $R^1$ are as defined above with magnesium oxide, magnesium methoxide or zinc oxide and a ligand such as, for example, tetramethylethylenediamine, tetrahydrofuran, pyridine, and the like in a solvent such as, for example, toluene, heptane, and the like, at about the reflux temperature of the solvent for about 30 minutes to about 2 hours to afford a compound of Formula III. Preferably the reaction is carried out in toluene at reflux for one hour.

A compound of Formula IV wherein X is a halogen such as, for example, bromide, chloride, and the like and R and $R^1$ are as defined above is prepared by reacting a compound of Formula V wherein R and $R^1$ are as defined above with anhydrous magnesium chloride or magnesium bromide in the presence of a solvent such as, for example, tetrahydrofuran, and the like at about the reflux temperature of the solvent for about 30 minutes to about 4 hours to afford a compound of Formula IV. Preferably, the reaction is carried out in tetrahydrofuran at reflux for 2 hours. Alternatively, a compound of Formula IV may be prepared by reacting a compound of Formula VI

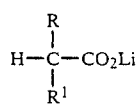 VI wherein R and $R^1$ are as defined above with anhydrous magnesium chloride or magnesium bromide in the presence of a solvent such as, for example, tetrahydrofuran, and the like at a temperature of about 25° C. to about the reflux temperature of the solvent for about 5 minutes to about 1 hour to afford a compound of Formula IV. Preferably, the reaction is carried out in tetrahydrofuran at 50° C. for 5 to 15 minutes.

Compounds of Formulas III, IV and VI may be isolated and subsequently purified, if desired, or used directly without isolation in the subsequent reaction with a compound of Formula II in the case of compounds of Formulas III or IV and a compound of Formula IV in the case of a compound of Formula VI.

A compound of Formula I wherein $R^2$ is lower alkyl, aryl, or aryloxy, n is zero or an integer of one to six and R and $R^1$ are as defined above is prepared by reacting either a compound of Formula III or a compound of Formula IV with a compound of Formula II wherein $R^3$ is a leaving group such as, for example, halogen for example chlorine, bromine and the like, para-toluenesulfonyl, methanesulfonyl, trifluoromethanesulfonyl, and the like and $R^2$ and n are as defined above in the presence of an alkali amide such as, for example, lithium diethylamide, lithium diisopropylamide, lithium tertiary butylamide, lithium n-dibutylamide, lithium diisobutylamide, lithium cyclohexyl isopropyl amide, and the like and a solvent such as, for example, toluene and the like at a temperature of about 25° C. to about the reflux temperature of the solvent for about 20 minutes to about 24 hours to afford a compound of Formula I. Preferably, the reaction is carried out in toluene at 50° C. for 12 to 18 hours.

A compound of Formula I is isolated by conventional procedures. Thus, at the completion of the alkylation reaction, water and 6N hydrochloric acid solution are added. The phases separated and the aqueous phase back-extracted with a water immiscible solvent such as, for example, diethyl ether, hexane, and the like. The organic extracts are combined, washed with brine, dried with a drying agent such as, for example, magnesium sulfate, and the like, the solvent evaporated and the residue optionally distilled or recrystallized to afford a compound of Formula I. Additionally, if desired, the original organic layer may be evaporated and the residue stirred with 2N potassium hydroxide solution and a solvent such as, for example, diethyl ether, hexane, and the like. The potassium hydroxide layer is back-extracted with a water immiscible solvent as defined above, separated, acidified with 6N hydrochloric acid solution to Congo red and the acidic product isolated with the aforementioned solvent. The organic layer is separated, washed with brine, dried as previously described, the solvent evaporated and the residue optionally distilled or recrystallized to afford an additional quantity of a compound of Formula I.

A compound of Formula VI is prepared by reacting a compound of Formula V with lithium hydroxide in the presence of a solvent such as, for example, toluene, and the like and removing water by azeotropic distillation to afford a compound of Formula VI.

Compounds of Formula II are either known or capable of being prepared by methods known in the art.

The following nonlimiting examples illustrate the inventor's preferred methods for preparing the compounds of the invention.

EXAMPLE 1

5-(2,5-Dimethylphenoxy)-2,2-dimethylpentanoic acid
Method A

A mixture of 17.6 g (200 mmol) of isobutyric acid, 4.0 g (100 mmol) of magnesium oxide and 12.8 g ($1.1 \times 100$ mmol) of tetramethylethylenediamine in 200 mL of toluene is stirred at reflux for 2 hours. Water evolution is complete within 30 minutes. The cooled solution is filtered through a thin pad of celite to remove a small quantity of magnesium oxide, then the toluene is removed on a rotary evaporator leaving the magnesium complex as a viscous oil. A 1-L flask is flushed with nitrogen and charged with 22.2 g (220 mmol) of diisopropylamine and 200 mL of anhydrous tetrahydrofuran (freshly distilled from sodium aluminum hydride under nitrogen). The solution is cooled to 0° C. and 145 mL of a standard solution of n-butyllithium in hexane (1.55 M; 220 mmol) is added by injection at a temperature <10° C. The solution is stirred briefly, then a solution of the magnesium isobutyrate complex in 100 mL toluene is added over 10 minutes. A homogeneous solution is obtained. The solution is stirred at 30°-35° C. for 1 hour during which time a small quantity of the metalated intermediate separates as a white solid. Finally, 48.6 g (200 mmol) of 2-(3-bromopropoxy)-1,4-dimethylbenzene in a small volume of toluene is added at ambient temperature over 15 minutes. No exothermic reaction is detected. At the conclusion of the addition, the temperature is increased to 50° C. The temperature increased to 65° C. After stirring at 50° C. for 18 hours, 200 mL of water is added at a temperature <10° C. The initial aqueous and organic layers are homogeneous. Hexane, 100 mL, and 100 mL of water are added and a heterogeneous lower phase develops. After standing, the aqueous layer is combined with the initial aqueous layer and the heterogeneous solution is acidified to Congo red with 6N hydrochloric acid solution and the product is isolated with diethyl ether. The diethyl ether solution is washed with brine, dried (magnesium sulfate), and evaporated leaving 41.8 g of product which crystallizes on standing.

The original organic layer is evaporated and the residue is stirred with 100 mL of 2N potassium hydroxide solution and diethyl ether. The potassium hydroxide layer is back-extracted with diethyl ether, then acidified with 6N hydrochloric acid solution to Congo red and the acidic product isolated with diethyl ether. The diethyl ether extracts are washed with brine, dried (magnesium sulfate) and evaporated leaving 3.9 g of product. Combined product $41.8 + 3.9 = 45.7$ g.

Recrystallization from 100 mL acetonitrile (charcoal) affords 29.7 g of 5-(2,5-dimethylphenoxy)-2,2-dimethylpentanoic acid as a colorless solid; mp 60°-61° C. Evaporation of the filtrate and distillation of the residue through a short path apparatus affords 9.6 g; bp 157°-159° C./0.5 mm. Combined yield is 39.3 g.

Method B

A 1-L flask is flushed with nitrogen and charged with 21.2 g (210 mmol) of diisopropylamine and 200 mL of anhydrous tetrahydrofuran (distilled from sodium aluminum hydride under nitrogen). The solution is cooled in an ice-salt bath and 105 mL of a standard solution of n-butyllithium in hexane (2.0 M; 210 mmol) is added by injection at a temperature <10° C. The solution of lithium diisopropylamide is stirred briefly at 0° C.; then 12.0 g (50 mmol) of zinc isobutyrate (Example A) is added in one portion. An exothermic reaction causes a temperature increase to 15° C. The homogeneous solution is stirred for 15 minutes, then the ice bath is removed and the solution is stirred at ambient temperature for 30 minutes. The ice bath is replaced and 24.3 g (100 mmol) of 2-(3-bromopropoxy)-1,4-dimethylbenzene in a small volume of toluene is added at 0°-10° C. over 15 minutes. The ice bath is retained for 15 minutes, then the temperature is maintained at 35° C. for 18 hours overnight.

At the conclusion of the reaction period 150 mL of water is added at a temperature <10° C. and the organic phase is stirred with 50 mL of water. The heterogeneous aqueous layers are combined (suspended ZnO), back-extracted with diethyl ether, then acidified to Congo red with 6N hydrochloric acid solution and the product is isolated with diethyl ether. The diethyl ether solution is washed with brine, dried (magnesium sulfate) and evaporated leaving 21.0 g of crude product which crystallizes on standing.

The original organic layers are combined, dried (magnesium sulfate), and evaporated. The residue is taken up in diethyl ether and stirred with $2 \times 50$ mL 1N potassium hydroxide solution. The base layers are combined, back-extracted with diethyl ether, acidified with hydrochloric acid solution and acidic material is isolated with diethyl ether. The diethyl ether solution is washed with brine, dried (magnesium sulfate), and evaporated leaving 0.5 g of a residual oil which crystallizes on standing. Combined yield: $21.0$ g $+0.5$ g $=21.5$ g.

Recrystallization from 50 mL of acetonitrile yields after refrigeration 11.2 g of 5-(2,5-dimethylphenoxy)-2,2-dimethylpentanoic acid as colorless crystals; mp 59.5°-60.5° C. Evaporation of the filtrate and distillation of the residue through a short path apparatus affords 6.6 g. Combined yield is 17.8 g.

Method C

A mixture of 8.8 g (100 mmol) of isobutyric acid, 4.1 g (50 mmol) of zinc oxide, and 7.9 g ($1.1 \times 100$ mmol) of tetrahydrofuran in 150 mL toluene is stirred at reflux for 6 hours beneath a phase separating head. Water evolution is complete within 1 hour. The warm solution (ca 50° C.) is filtered through a thin pad of celite to remove a small quantity of insoluble solid. The toluene solution is concentrated to 100 mL. A 500-mL flask is flushed with nitrogen, then charged with 20.2 g (200 mmol) of diisopropylamine and 50 mL anhydrous tetrahydrofuran (distilled from sodium aluminum hydride under nitrogen). The solution is cooled to 0° C. and 100 mL of a standard solution of n-butyllithium in hexane (2.0 M; 200 mmol) is added by injection at a temperature <10° C. The solution is stirred briefly then a solution of the previously prepared zinc isobutyrate complex in 100 mL of toluene is added over 10 minutes at a temperature ≦10° C. A slightly turbid solution is produced. The solution is stirred at 25°–30° C. for 1 hour, then 24.3 g (100 mmol) of 2-(3-bromopropoxy)-1,4-dimethylbenzene in a small volume of toluene is added at ambient temperature over 10 minutes. A mild exothermic reaction results which ultimately carries the temperature to 42° C. (temperature change: 25°→42° C.) over a 10-minute period. When the temperature subsides to 35° C. a temperature regulator is attached to a heating mantle and the solution (slightly turbid) is stirred at 50° C. for 18 hours overnight.

The slightly turbid solution is cooled (<10° C.) and 100 mL of water is added cautiously. The organic layer is washed with 50 mL of water and the aqueous layers ar combined. After acidifying with 40 mL of 6N hydrochloric acid solution the product is isolated with diethyl ether. The diethyl ether solution is washed with brine, dried (magnesium sulfate), and evaporated leaving 22.1 g of 5-(2,5-dimethylphenoxy)-2,2-dimethylpentanoic acid which crystallizes on standing.

The original organic layer is evaporated and the residue is stirred with diethyl ether and 2×50 mL of 1N potassium hydroxide solution. The aqueous layers are combined, back extracted with diethyl ether, acidified with excess 6N hydrochloric acid solution (20 mL), and the acidic product is isolated with diethyl ether. The diethyl ether solution is washed with brine, dried (magnesium sulfate), and evaporated affording 0.3 g of product. Combined yield is 22.4 g. Recrystallization from 50 mL of acetonitrile yields after refrigeration 10.3 g of product, mp 58°–59.5° C. Evaporation of the filtrate and distillation of the residue through a short path apparatus affords 6.6 g of product. Combined yield is 16.9 g.

EXAMPLE 2

2-Propylpentanoic acid

A 1-L flask is charged with 6.0 g (150 mmol) of magnesium oxide, 23.7 g (300 mmol) of pyridine, 250 mL of toluene and 30.6 g (300 mmol) of valeric acid. The mixture is stirred at reflux for three hours. A slightly turbid, homogeneous and highly mobile solution is produced. Water evolution (2.7 mL collected=theory) is complete within one hour. The toluene solution is concentrated by removing 100 mL of toluene by distillation, then 30.3 g (300 mmol) of diisopropylamine is added to the cooled solution and 180 mL of a standard solution of n-butyllithium in heptane (1.67 M; 300 mmol) is added by injection at 20°–25° C. in four equal 45 mL portions at 20–30 minute intervals. The solution turned yellow during addition of the initial quantities of each 45 mL portion of n-butyllithium; but the color dissipates rapidly with continued stirring.

A substantial precipitate is produced initially which partially dissolves upon addition of subsequent portions of n-butyllithium. The heterogeneous mixture is stirred at ambient temperature for one hour. Then 36.9 g (300 mmol) of 1-bromopropane is added at 22° C. over 10 minutes. On continued stirring the temperature gradually increases to 30° C. After one hour the mixture is warmed to 50° C. for 18 hours overnight. After the conclusion of the reaction period, 200 mL of 6N hydrochloric acid solution is added dropwise at a temperature <15°. Then 100 mL of water is added, the aqueous layer (acidified to Congo red) is extracted with diethyl ether. The organic layer is washed with brine, dried and evaporated. The colored residue is stirred with 150 mL then 2×50 mL of 2N potassium hydroxide solution. The base layers are back-extracted with diethyl ether, acidified to Congo red with excess 6N hydrochloric acid solution and the product is isolated with diethyl ether. The diethyl ether solution is washed with brine, dried (magnesium sulfate) and evaporated leaving 30.4 g of crude acids. Distillation through a 6" vacuum jacketed vigreux column affords 16.3 g of 2-propylpentanoic acid; bp 83°–93° C./2 mm.

EXAMPLE 3

2,2-Dimethylhexanoic acid

Method A: Magnesium Methoxide Procedure

A 2-L flask is charged with 4.9 g (200 g-atom) of magnesium turnings, 75 mL of methanol and a crystal of iodine. The mixture is heated to reflux until all the magnesium has reacted leaving a grey slurry of magnesium methoxide. After cooling, 35.2 g (400 mmol) of isobutyric acid is added followed by 250 mL of toluene. A condenser is attached set for downward distillation and the methanol and some toluene are distilled until 250 mL of distillate is collected and the distillation temperature reaches ~110° C. The mixture is cooled, 400 mL of anhydrous tetrahydrofuran is added along with 41 g (400 mmol) of diisopropylamine ad the resulting homogeneous solution is cooled in an ice bath. Finally, 240 mL of a standard solution of n-butyllithium in heptane (1.67 mmol/mL; 400 mmol) is added by injection at a temperature <10° C. The ice bath is retained for 10 minutes and then the mixture is warmed to 30°–35° C. for 30 minutes to complete the metalation. The ice bath is replaced and 54.8 g (400 mmol)) of 1-bromobutane is added over 15 minutes at 0° C. No exothermic reaction is observed. The ice bath is retained for 30 minutes and then the mixture is heated to 30°–35° C. for 18 hours overnight. At the conclusion of the reaction period, 150 mL of 6N hydrochloric acid solution (0.90 mmol)) is added at a temperature <10° C. followed by 280 mL of water. The aqueous layer is separated extracted with 200 mL of diethyl ether and the combined organic layers ar washed with 150 mL of 2N hydrochloric acid solution, 200 mL of saturated sodium chloride, dried (magnesium sulfate) and evaporated. This affords 64 g of product. Distillation through a 6" vacuum jacketed vigreux column affords 42.7 g of 2,2-dimethylhexanoic acid; $bp_D$ 103°–105°/5 mm; $n^{25}$ 1.4245.

Method B₁: Lithium Hydride-Magnesium Halide Procedure

A 1-L flask is charged with 2.6 g (330 mmol) of lithium hydride, 14.3 g (150 mmol) of anhydrous magnesium chloride, 31 g (300 mmol) of dry diisopropylamine and 300 mL of tetrahydrofuran (mixture bubbles gently—evolving hydrogen before addition of isobutyric acid). To the stirred mixture is added 26.4 g (300 mmol) of isobutyric acid at a temperature <25° C. When the addition is complete, the mixture is heated to reflux for approximately two hours during which time the hydrogen evolution ceases. The mixture is cooled and 180 mL of a standard solution of n-butyllithium in heptane (1.67 M; 300 mmol) is added at a temperature <10° C. The mixture is warmed to 30°–35° C. for two hours to afford a heterogeneous mixture consisting of a substantial finely divided precipitate that does not completely separate when stirring is stopped. The mixture is cooled and 41.1 g (300 mmol) of 1-bromobutane is added over 15 minutes. A slight exothermic reaction results in a temperature increase from 30°–34° C. during the addition. The mixture is then warmed to 35° C. for 18 hours. Then 900 milliequivalents of 3 N hydrochloric acid solution is added at a temperature <15° C. The organic layer is separated and the aqueous layer is extracted with 100 mL of diethyl ether. The organic layers are combined, washed with 100 mL of water. Then the solution is stirred with 150 mL of 2N potassium hydroxide solution and then 100 mL of 2N potassium hydroxide solution. The potassium hydroxide layers are combined, extracted with 100 mL of diethyl ether, acidified to Congo red with excess 6N hydrochloric acid solution and the product is isolated with diethyl ether. The diethyl ether layer is separated, washed with brine, dried, and evaporated to afford 43 g of product. Distillation affords 36.6 g of 2,2-dimethylhexanoic acid; bp 102°–105° C./5 mm; $n_D^{25}$ 1.4245. The process described in Method B$_1$ may be varied as follows:

Method B$_2$

When diisopropylamine is added after isobutyric acid in Method B$_1$, followed by n-butyllithium, a slightly heterogeneous solution of metalated magnesium isobutyrate is obtained. After addition of 1-bromobutane and workup as previously described, 50 g of product is obtained. Distillation as previously described affords 36.3 g of 2,2-dimethylhexanoic acid; bp 102°–106° C./5 mm; $n_D^{25}$ 1.4241.

Method B$_3$

If the reaction between lithium hydride, magnesium chloride, and isobutyric is maintained below 35° C. for 4 days before addition of diisopropylamine and n-butyllithium, a homogeneous solution of metalated magnesium isobutyrate is obtained. Addition of 1-bromobutane and workup as previously described affords 38.5 g of product. Distillation as previously described affords 30.6 g of 2,2-dimethylhexanoic acid; bp 103°–105° C./5 mm; $n_D^{25}$ 1.4244.

Alternative Method B: Using a Lithium Carboxylate Preparation of 2-Propylpentanoic acid

Step A: Preparation of Lithium Valerate

A solution of 42.0 g (1.00 mol) of lithium hydroxide monohydrate in 175 mL of water is placed in a 2-L flask fitted with a stirrer and condenser interrupted by a Barrett trap. To the solution is added 102.1 g (1 mol) of valeric acid and 700 mL of toluene. The heterogeneous mixture is stirred at reflux for 8 hours to remove all of the water by azeotropic distillation. When most of the water has been removed, some foaming occurs which carries some of the salt into the condenser. After cooling the salt is collected, washed with fresh toluene and dried in vacuo at 90° C. for 3 hours. The fine powder amounted to 103 g of lithium valerate.

Anal. calculated for C$_5$H$_9$O$_2$Li: C, 55.57; H, 8.40, Found: C, 55.78; H, 8.40, Karl Fischer (water)=0.00

Step B: Preparation of 2-propylpentanoic acid

A 2-L flask is charged with 21.6 g (200 mmol) of lithium valerate, 9.5 g (100 mmol) of anhydrous magnesium chloride and 250 mL anhydrous tetrahydrofuran (freshly distilled from sodium, benzophenone). The stirred mixture is warmed to 50° C. allowing the metathetical exchange to occur and a homogeneous solution is produced within 5–15 minutes. The slightly hazy solution is cooled and 5.1 g (200/4 mmol) of diisopropylamine is added. Some precipitate forms and continued stirring fails to effect solution. Finally, 120 mL of a standard solution (1.67M; 200 mmol) of n-butyllithium in heptane is added in four portions at 15-minute intervals at 25°–30° C. After addition of the first portion, a homogeneous solution is produced but addition of the remaining portions yields a turbid mixture. After addition of the final portion, the mixture is permitted to stir for 2 hours at ambient temperature. Then the heterogeneous mixture is cooled to 0° C. and 24.6 g (200 mmol) of 1-bromopropane is added over 10 minutes. Finally, the mixture is warmed to 50° C. for 12 hours overnight. At the conclusion of the reaction period, the mixture is cooled and 200 mL of 6N hydrochloric acid solution is added at a temperature <15° C. followed by 100 mL of water. The phases are separated and the aqueous layer is back-extracted with 100 mL of diethyl ether. The organic layers are combined and the solution is washed with brine, dried (magnesium sulfate), evaporated and the residue is distilled through a 6" heated helices packed column to afford 6.5 g of 2-propylpentanoic acid; bp 89°–92° C./2 mm.

Preparation of Staring Materials

EXAMPLE A

Zinc Isobutyrate

A 500-mL flask is equipped with a spin bar, then charged with 17.7 g (200 mmol) of isobutyric acid, 8.1 g (100 mmol) of zinc oxide, and 200 mL of toluene. A homogeneous solution is produced when the mixture is stirred at reflux beneath a phase separating head. Water evolution is complete within 30 minutes.

The solution is cooled and the crystalline product is collected and washed with toluene and dried in vacuo, yielding 22.2 g of zinc isobutyrate; m.p. 230°–233° C.

What is claimed is:

1. A process for the preparation of a compound of Formula I

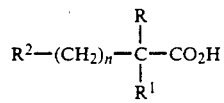

wherein R is hydrogen, lower alkyl, lower alkoxy, or aryl;
R$^1$ is hydrogen or lower alkyl;
R$^2$ is lower alkyl, aryl or aryloxy; and
n is zero or an integer of one to six which comprises:
(a) reacting a compound of Formula V

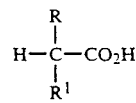

wherein R and R¹ are as defined above with magnesium oxide, magnesium methoxide, or zinc oxide and a ligand in a solvent to afford a compound of Formula III

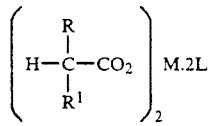     III wherein M is magnesium or zinc, L is a ligand and R and R¹ are as defined above which may optionally be isolated if desired;

(b) reacting a compound of Formula III with a compound of Formula II $$R^2-(CH_2)_n-R^3 \qquad II$$

wherein R³ is a leaving group and R² and n are as defined above in the presence of an alkali amide to afford, after conventional isolation, a compound of Formula I.

2. A process for the preparation of a compound of Formula I

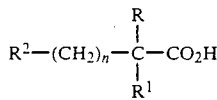     I wherein R is hydrogen, lower alkyl, lower alkoxy, or aryl;

R¹ is hydrogen or lower alkyl;

R² is lower alkyl, aryl or aryloxy; and n is zero or an integer of one to six which comprises:

(a) reacting a compound of Formula V

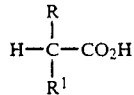     V wherein R and R¹ are as defined above with magnesium bromide and lithium hydride or magnesium chloride and lithium hydride in a solvent to afford a compound of formula IV

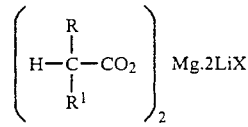     IV wherein X is bromide or chloride and R and R¹ are as defined above, which may optionally be isolated if desired:

(b) reacting a compound of Formula IV with a compound of Formula II $$R^2-(CH_2)_n-R^3 \qquad II$$

wherein R³ is a leaving group and R² and n are as defined above in the presence of an alkali amide to afford, after conventional isolation, a compound of Formula I.

3. A process according to claim 1 wherein the ligand in step (a) is selected from the group consisting of tetramethylethylenediamine, tetrahydrofuran and pyridine.

4. A process according to claim 3 wherein the ligand in step (a) is tetramethylethylenediamine.

5. A process according to claim 1 wherein the alkali amide in step (b) is selected from the group consisting of lithium diethylamide, lithium diisopropylamide, lithium tertiary butylamide, lithium n-dibutylamide, lithium diisobutylamide and lithium cyclohexyl isopropyl amide.

6. A process according to claim 5 wherein the alkali amide in step (b) is lithium diisopropylamide.

7. A process according to claim 1 wherein R and R¹ are lower alkyl; R² is aryloxy; and n is three.

8. A process according to claim 7 wherein R and R¹ are methyl.

9. A process according to claim 8 and for the preparation of 5-(2,5-dimethylphenoxy)-2,2-dimethylpentanoic acid.

10. A process according to claim 2 wherein the alkali amide in step (b) is selected from the group consisting of lithium diethylamide, lithium diisopropylamide, lithium tertiary butylamide, lithium n-dibutylamide, lithium diisobutylamide and lithium cyclohexyl isopropyl amide.

11. A process according to claim 10 wherein the alkali amide in step (b) is lithium diisopropylamide.

12. A process according to claim 2 wherein R and R¹ are lower alkyl; R² is aryloxy; and n is three.

13. A process according to claim 12 wherein R and R¹ are methyl.

14. A process according to claim 13 and for the preparation of 5-(2,5-dimethylphenoxy)-2,2-dimethylpentanoic acid.

* * * * *